US008801632B2

(12) United States Patent
Chan

(10) Patent No.: US 8,801,632 B2
(45) Date of Patent: Aug. 12, 2014

(54) STACK MAGAZINE SYSTEM

(75) Inventor: Frank A. Chan, Sunnyvale, CA (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 172 days.

(21) Appl. No.: 13/470,694

(22) Filed: May 14, 2012

(65) Prior Publication Data
US 2012/0226115 A1 Sep. 6, 2012

Related U.S. Application Data

(62) Division of application No. 12/699,204, filed on Feb. 3, 2010, now Pat. No. 8,197,422, which is a division of application No. 11/275,739, filed on Jan. 26, 2006, now Pat. No. 7,708,702.

(51) Int. Cl.
A61B 5/00 (2006.01)
B65D 81/00 (2006.01)
A61B 5/151 (2006.01)
G01N 33/487 (2006.01)

(52) U.S. Cl.
CPC ...... A61B 5/15174 (2013.01); G01N 33/48757 (2013.01)
USPC .......................................... 600/583; 600/584

(58) Field of Classification Search
CPC .. A61B 5/1405; A61B 5/1411; A61B 5/1427; A61B 5/151; A61B 5/15101; A61B 5/15142; A61B 5/15146; A61B 5/15186; G01N 33/48757
USPC ........................... 600/583–584; 606/181–182
See application file for complete search history.

(56) References Cited

U.S. PATENT DOCUMENTS 5,097,938 A 3/1992 Gruner et al.
5,744,098 A 4/1998 Kratzer et al.
(Continued)

FOREIGN PATENT DOCUMENTS

DE 42 34 553 A1 4/1993
EP 0 826 963 A2 3/1998
(Continued)

OTHER PUBLICATIONS

European Patent Application No. 07 703 010.4 Examination Report mailed Oct. 6, 2010.
(Continued)

Primary Examiner — Max Hindenburg
Assistant Examiner — Adam Eiseman
(74) Attorney, Agent, or Firm — Woodard, Emhardt, Moriarty, McNett & Henry LLP

(57) ABSTRACT

A meter system for analyzing body fluids includes a supply magazine for storing a stack of test elements, a meter for analyzing fluid samples, and a transport system for transporting test elements from the supply magazine to the meter. The test element in one embodiment includes a lancet integrated test element that has a lancet coupled to a test strip. The transport system is configured to minimize damage to the test element. In one form, the transport system includes a shuttle that slides the top-most test element from the stack onto a connection portion of the meter. In another form, the transport system includes a drum that rotates to transport test elements from the supply magazine to a testing position and, once used, to a waste magazine for disposal. In a further form, the transport system includes a disc that rotates to transport the test elements.

8 Claims, 9 Drawing Sheets

(56) References Cited

U.S. PATENT DOCUMENTS

| | | | |
|---|---|---|---|
| 5,971,941 A * | 10/1999 | Simons et al. | 600/573 |
| 6,036,924 A | 3/2000 | Simons et al. | |
| 6,159,424 A | 12/2000 | Kauhaniemi et al. | |
| 6,827,899 B2 | 12/2004 | Maisey et al. | |
| 2002/0052618 A1 | 5/2002 | Haar et al. | |
| 2002/0057933 A1 | 5/2002 | Ebihara et al. | |
| 2002/0076349 A1 | 6/2002 | Aitken et al. | |
| 2003/0002387 A1 | 1/2003 | Bottwein et al. | |
| 2003/0083685 A1 | 5/2003 | Freeman et al. | |
| 2003/0191415 A1 | 10/2003 | Moerman et al. | |
| 2003/0199789 A1 | 10/2003 | Boecker et al. | |
| 2003/0199895 A1 | 10/2003 | Boecker et al. | |
| 2003/0212423 A1 | 11/2003 | Pugh et al. | |
| 2004/0138688 A1 | 7/2004 | Giraud | |
| 2005/0095173 A1 | 5/2005 | Matsumoto | |
| 2005/0143675 A1 | 6/2005 | Neel et al. | |
| 2005/0234368 A1 | 10/2005 | Wong et al. | |
| 2008/0167578 A1 * | 7/2008 | Bryer et al. | 600/583 |
| 2008/0267822 A1 * | 10/2008 | List et al. | 422/68.1 |

FOREIGN PATENT DOCUMENTS

| | | |
|---|---|---|
| EP | 1 321 769 A1 | 6/2003 |
| EP | 1 362 551 A | 11/2003 |
| WO | WO 94/10558 A1 | 5/1994 |
| WO | WO 01/00090 A1 | 1/2001 |
| WO | WO 02/08753 A2 | 1/2002 |
| WO | WO 02/18940 A2 | 3/2002 |
| WO | WO 03/082092 A1 | 10/2003 |
| WO | WO 2004/060174 A2 | 7/2004 |

OTHER PUBLICATIONS

International Patent Application PCT/EP2007/000608 Partial Search Report mailed Apr. 11, 2007.

U.S. Appl. No. 11/070,502, filed Mar. 2, 2005 to Roe.

* cited by examiner

STACK MAGAZINE SYSTEM

CROSS-REFERENCE TO RELATED APPLICATION

This application is a divisional of U.S. patent application Ser. No. 12/699,204, filed Feb. 3, 2010 now U.S. Pat. No. 8,197,422, which is a divisional of U.S. patent application Ser. No. 11/275,739, filed Jan. 26, 2006 now U.S. Pat. No. 7,708,702, which are hereby incorporated by reference.

BACKGROUND

The present invention generally relates to bodily fluid sampling devices and more specifically, but not exclusively, concerns a dispenser system for dispensing test elements that test biological fluid.

The acquisition and testing of bodily fluids is useful for many purposes and continues to grow in importance for use in medical diagnosis and treatment, such as for diabetes, and in other diverse applications. In the medical field, it is desirable for lay operators to perform tests routinely, quickly, and reproducibly outside of a laboratory setting, with rapid results and a readout of the resulting test information. Testing can be performed on various bodily fluids and, for certain applications, is particularly related to the testing of blood and/or interstitial fluid. Performing home-based testing can be difficult for many patients, especially for patients with limited hand dexterity, such as the elderly or diabetics. For example, diabetics can sometimes experience numbness or tingling in their extremities, such as their hands, which can make self-testing difficult because they are unable to accurately position a test strip to collect the blood sample. In addition, wounds for diabetics tend to heal more slowly, and as a result, there is a desire to make incisions less invasive.

Recently, lancet integrated test strips or elements have been developed in which a test strip is integrated with a lancet or other piercing means so as to form a single disposable unit. While these integrated units have somewhat simplified the collection and testing of fluid samples, there are still a number of issues that need to be resolved before a commercial unit can be implemented. One issue concerns maintaining the sterility of the lancet prior to use so as to minimize the risk of infection. Another issue concerns the disposal of used units after use. Once used, the integrated units become a biohazard that need to be disposed of in a safe manner. A number of different types of systems have been proposed for dispensing test strips, lancets, or some combination thereof, but most of these systems have significant drawbacks.

Multiple use test systems like drums, discs, and reel-to-reel tapes have been developed to house multiple test strips, but these systems fail to address a number of issues. For example, reel-to-reel cassette systems typically bend a tape of lancet integrated test elements during dispensing, which can result in damage to the lancet and/or the test strip. Other cassette or cartridges are bulky in nature, which makes them commercially impractical for household or other routine use. Still yet other systems require the use of a complicated indexing mechanism, which tends to make the systems have an unsuitable reliability due to jamming and/or other complications. Typically, such systems also require specially designed test elements that are not configured for current single use test strips. Drum transport systems have been proposed for transporting test strips from a magazine, but such drum transport systems have failed to satisfactorily address the disposal issue regarding the used test strips.

With portable meters, such as portable blood glucose meters, small meter sizes and ease of handling are desirable features. Most users would prefer smaller meters that are able to discretely fit inside a pocket or a purse so that the user is able to perform testing in any situation, such as in a restaurant bathroom or when traveling. One factor affecting size of meters that handle multiple test strips is storage compartment sizes. In previous designs, the storage compartments tended to be rather large and bulky because test elements were stored in a disorderly fashion.

Thus, needs remain for further contributions in this area of technology.

SUMMARY

One aspect concerns a meter system that includes a supply magazine that stores a plurality of lancet integrated test elements in a stacked manner. The lancet integrated test elements each include a test strip for testing a body fluid sample and a lancet. The test strip is generally flat, and the test strip has a sample opening at one end and opposing side edges. The lancet is coupled to the test strip for forming an incision where the body fluid sample is drawn. The lancet is configured to extend proximal the sample opening. A meter has a connector portion configured to operatively couple to the lancet integrated. The meter is configured to fire the lancets on the lancet integrated test elements. A transport mechanism is configured to transfer the lancet integrated test elements to the connector portion of the meter. The transport mechanism is configured to engage at least one of the side edges to minimize risk of damaging the test strip and lancet proximal the sample opening of the lancet integrated test element.

Another aspect concerns a system that includes a supply magazine configured to store test elements in a stacked manner prior to use. The test elements are configured to analyze body fluid. A waste magazine is configured to store the test elements in a stacked manner after use. A transport drum is disposed between the supply magazine and the waste magazine to transport the test elements from the supply magazine to the waste magazine.

Still yet another aspect concerns a system that includes a supply magazine configured to store a stack of test elements. A meter includes a connector configured to connect to the test elements. A transport system is configured to transport test elements from the supply magazine to the connector of the meter. The transport system includes a disc-shaped transport member configured to receive at least one of the test elements from the magazine. The disc-shaped transport member is rotatable relative to the meter to transport the at least one of the test elements to the connector.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
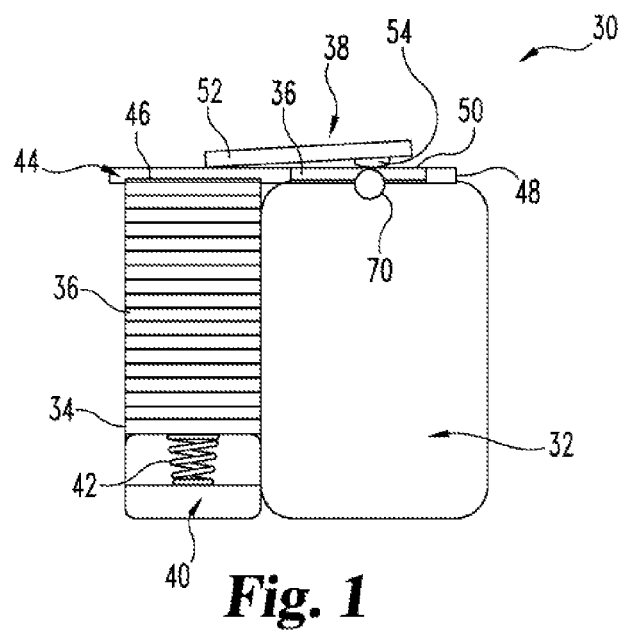
FIG. 1 is a front view of a meter system according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. A number of embodiments of the invention are shown in detail; although it will be apparent to those skilled in the relevant art that some features that are not relevant to the present invention may not be shown for the sake of clarity. It should be noted that directional terms, such as "up", "down", "top" and "bottom", are used herein solely for the convenience of the reader in order to aid in the reader's understanding of the illustrated embodiments, and it is not the intent that the use of these directional terms in any manner limit the described, illustrated, and/or claimed features to a specific direction or orientation.

As mentioned previously, there have been a number of drawbacks to prior cartridge or cassette designs, especially with respect to lancet integrated test elements (LITs). For example, some cassette systems bend a tape of LITs during dispensing, which can result in damage to the lancet and/or the test strip. Other cassette or cartridges are bulky in nature, which makes them commercially impractical for household or other routine use. Still yet other systems require the use of a complicated indexing mechanism, which tends to make the systems have unsuitable reliability due to jamming and/or other problems. Typically, such systems also require specially designed test elements that are not configured for current single use test strips. Moreover, disposal of hazardous, used LITs is always a concern.

The meter system according to a number of aspects of the present invention addresses these as well as many other concerns. A meter system for analyzing body fluids includes a supply magazine for storing a stack of test elements, a meter for analyzing fluid samples, and a transport system for transporting test elements from the supply magazine to the meter. In a number of embodiments, the transport system is configured to minimize damage to the test elements as well as to promote fluid collection by grabbing the side edges of the test elements. Moreover, the transport systems limit the number of components used, which improves reliability as well as provides a compact design. The stack cartridge design allows for the use of preexisting single use test elements in a multiuse design. In one form, the transport system includes a shuttle that slides the top-most test element from the stack onto a connection portion of the meter. In another form, the transport system includes a drum that rotates to transport test elements from the supply magazine to a testing position and, once used, to a waste magazine for disposal. This allows used LITs to be disposed of safely. In a further form, the transport system includes a disc that rotates to transport the test elements. The disc-shaped transport system provides a compact and highly reliable design.

A meter transport system 30 according to one embodiment, among many, is depicted in FIGS. 1, 2, 3 and 4. As shown in FIG. 1, the system 30 includes a meter 32, a magazine 34 that contains a stack of test elements 36, and a transfer or transport mechanism 38 that transports the test elements 36 from the magazine 34 to the meter 32. In the illustrated embodiment, the test elements 36 include LITs that each include a lancet and a test strip. LITs are configured to lance an incision in tissue and analyze a body fluid sample from the incision. For further information regarding the LITs, reference is made to U.S. patent application Ser. No. 11/070,502, filed Mar. 2, 2005, which is incorporated by reference in its entirety. Nevertheless, the test element 36 in other embodiments can include other types of test elements, such as simple test strips that do not have any type of lancet or needle. The test elements 36 in the embodiment shown analyze fluid samples electrochemically, and the meter 32 is configured to analyze the signals from the test elements 36 so as to provide test results via a display or some other type of output device. However, in other embodiments, the test elements 36 and meter 32 can analyze fluid samples in other manners, such as optically.

Inside, the magazine 34 includes a molded desiccant 40 for maintaining low humidity levels within the magazine 34 and a spring 42 that is configured to bias the test elements 36 through an outlet opening of the magazine 34 into the transport mechanism 38. In one form, the spring 42 includes a coil spring, but it should be understood that the spring 42 can include other types of biasing devices. To further maintain acceptable humidity levels for the test elements 36 within the magazine 34, the magazine has a moisture seal 46 that seals the outlet opening 44, and the moisture seal 46 is removed prior to use.

Figure 2:
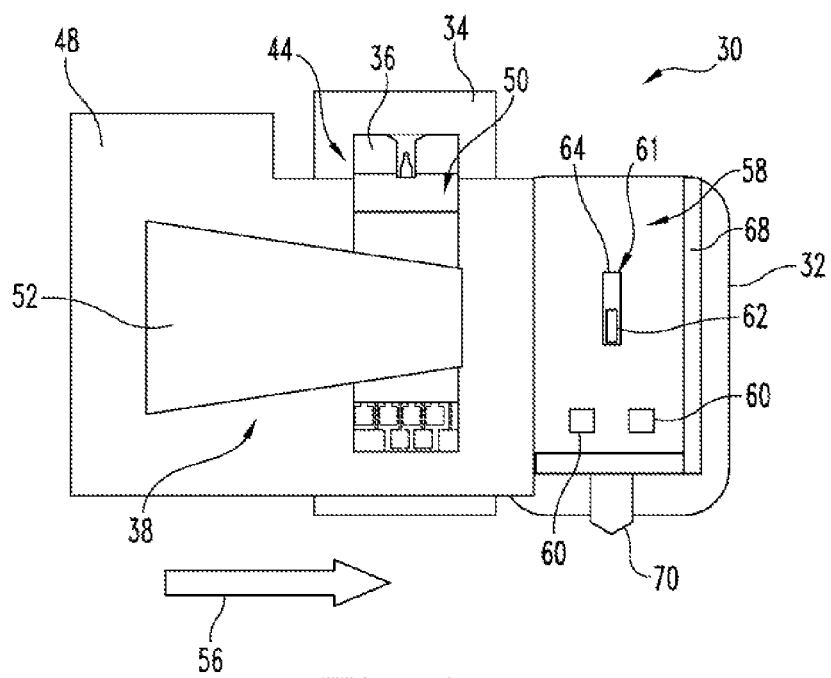
FIG. 2 is a first top view of the FIG. 1 meter system with a transport shuttle in a loading position.

Referring to FIG. 2, the transport mechanism 38 includes a transport member or shuttle 48 with a test element opening 50 in which the test elements 36 are received. The shuttle 48 in one embodiment is slidably coupled to the meter 32. In another embodiment, the shuttle 48 is slidably coupled to the magazine 34, and in further embodiments, the shuttle 48 is slidably coupled to both the meter 32 and the magazine 34. The transport mechanism 38 further includes a stabilizer arm 52 with a contact member 54 (FIG. 1) that contacts the test element 36 when positioned within the test element opening 50 of the shuttle 48. In the illustrated embodiment, the stabilizer arm 52 acts like a spring when pressing against the test element 36. In one form, the stabilizer arm 52 includes a leaf spring, but it should be recognized that the stabilizer arm 52 can include other types of biasing devices. The stabilizer arm 52 is configured to hold the test elements 36 within the test element opening 50. In particular, the stabilizer arm 52 applies a force to the test element 36 that is less than the force the spring 42 applies to the test elements 36 within the magazine 34 so that the magazine 34 is able to feed test elements 36 into the test element opening 50 of the shuttle 48.

Once the test element 36 is loaded, the shuttle 48 slides in a loading direction towards the meter 32, as is indicated by arrow 56 in FIG. 2. The motive force from the shuttle 48 is applied to the side edges of the test element 36, which tends to minimize the risk of damage. In one form, the user manually moves the shuttle 48, and in another form, the meter 32 automatically moves the shuttle 48 with a motor or other movement imparting device. The meter 32 has a load cavity 58 in which the test element 36 is loaded. In the illustrated embodiment, the load cavity 58 has one or more contacts 60 that electrically couple the test element 36 to the meter 32. Nevertheless, the contacts 60 can be located elsewhere or can be optional in other embodiments, such as for test elements that optically analyze samples. The load cavity 58 in the embodiment shown includes a lancet actuation mechanism 61 for firing the lancet in the test element 36. The lancet actuation mechanism 61 in one form is the same as the firing mechanism described in U.S. patent application Ser. No. 11/070,502, filed Mar. 2, 2005, which is incorporated by reference in its entirety. The lancet actuation mechanism 61 in FIG. 2 includes a lancet engagement arm 62 and a guide slot 64 where the lancet arm 62 moves during actuation. As should be recognized, other types of actuation or firing mechanisms can be used. Moreover, the lancet actuation mechanism 61 can be optional in other embodiments.

Figure 3:
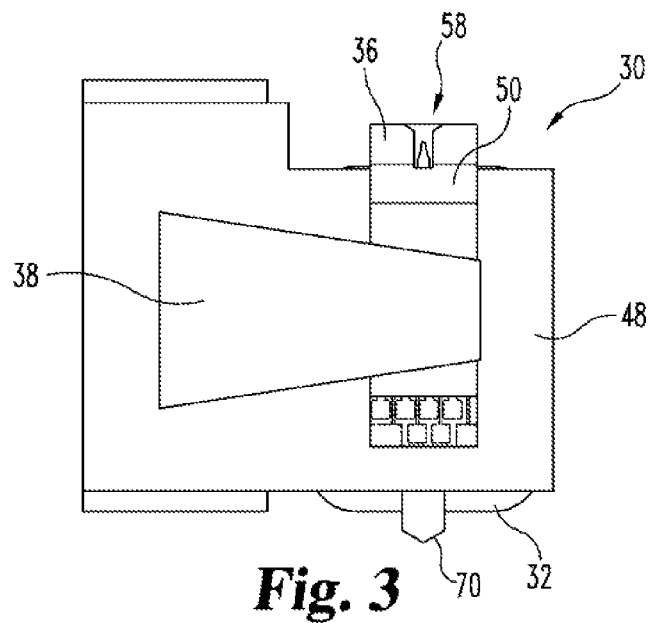
FIG. 3 is a second top view of the FIG. 1 meter system with the transport shuttle in an unloading position.

Looking again at FIG. 1, the surface between the ends of the magazine 34 and meter 32 along which the test element 36 rides when in the shuttle 48 are generally level or flush with one another. With the system of FIG. 1, the test element 36 can be accurately loaded into the meter 32, which can be important for test elements like LITs. If an LIT is improperly loaded, the lancet in the LIT can for example misfire and/or lance too deeply, which may lead to injury. When the test element 36 in the shuttle 48 slides over the load cavity 58 in the meter 32, as is shown in FIG. 3, the stabilizer arm 52 pushes the test element 36 into the load cavity 58, thereby loading the test element 36 on the meter 32. With such a construction, the location of the test element 36 can be tightly controlled. After the test element 36 is loaded, the lancet actuation mechanism is able to fire the lancet in the test element 36, and the meter 32 is able to read the test results from the test element 36 via contacts 60.

Figure 4:
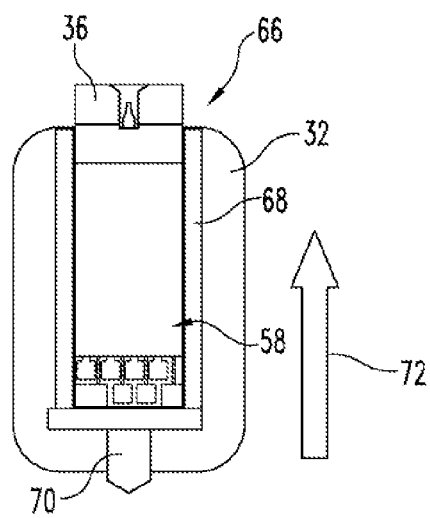
FIG. 4 is a top view of a lancet integrated test element loaded on a meter of the FIG. 1 system.

As can be seen in FIG. 4, which shows the top of the meter 32 with the shuttle 48 removed, an ejection mechanism 66 of the meter 32 defines the load cavity 58 in which the test element 36 is received. The ejection mechanism 66 includes a series of rails 68 that define the U-shaped load cavity 58 and an ejection button 70. The rails 68 are slidably mounted on the meter 32 such that when the user presses the ejection button 70, the test element 36 travels in an ejection direction, as is indicated with arrow 72 in FIG. 4. In one form, the ejection mechanism 66 is spring biased so that the ejection mechanism 66 returns to its initial position once the ejection button 70 is released. As should be recognized, the ejection mechanism 66 can be optional in other embodiments or can be automatically actuated.

The operation of the system 30 will be generally described with reference to FIGS. 1, 2, 3, and 4. Looking at FIGS. 1 and 2, the force applied by the spring 42 in the magazine 34 against the test elements 36 pushes a single test element 36 into the test element opening 50 of the shuttle 48. As the test element 36 is received into the shuttle 48, the stabilizer arm 52 deflects because the insertion force applied by the spring 42 in the magazine 34 is greater than the force applied by the stabilizer arm 52. The stabilizer arm 52 deflects to the extent so that a single test element 36 is received in the shuttle 48. It is envisioned that in other embodiments, the shuttle 48 can be configured to receive more than one test element 36. Once the test element 36 is loaded, the shuttle 48 slides in the loading direction 56 towards the meter 32. The shuttle 48 can be manually moved by the user and/or automatically moved by the meter 32.

When the shuttle 48 moves over the load cavity 58, the stabilizer arm 52 pushes the test element 36 into the load cavity 58, as is depicted in FIGS. 3 and 4. After the test element 36 is loaded, the lancet actuation mechanism 61 is used to fire the lancet in the test element 36. In one embodiment, the stabilizer arm 52 remains in contact with the test element 36 so that during lancing and/or fluid collection/analysis, the test element 36 remains stably positioned. In another embodiment, once the test element 36 is loaded, the shuttle 48 returns to the loading configuration that is illustrated in FIG. 2. After the incision is formed, the test element 36 collects the fluid sample, and the result from the fluid analysis in the meter 32 is communicated to the meter 32 via the contacts 60. Subsequently, the user ejects the now used test element 36 for disposal by pressing the ejection button 70 of the ejection mechanism 66.

Figure 5:
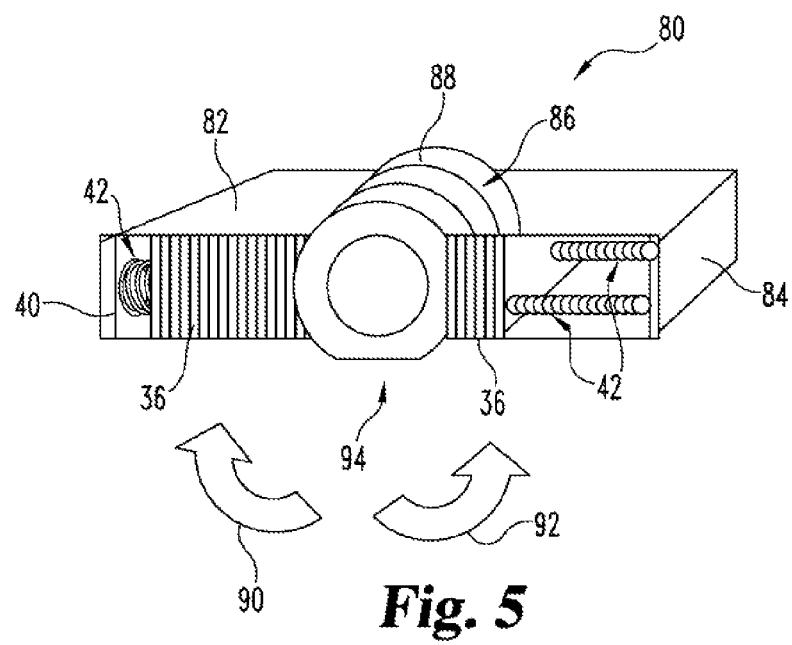
FIG. 5 is a perspective view of a meter system according to another embodiment.

A meter transport system 80 according to another embodiment is illustrated in FIG. 5. The meter transport system 80 is configured to be integrated with other components like a meter and a housing, for example. As can be seen, the meter system 80 in FIG. 5 includes a supply compartment or magazine 82 for storing unused test elements 36, a waste compartment or magazine 84 for storing used test elements 36, and a transfer or transport mechanism 86 that transports test elements 36 from the supply magazine 82 to the waste magazine 84. Both magazines 82, 84 include springs 42 for biasing the test elements 36 in the magazines 82, 84 so that the test elements 36 are tightly packed. The magazines 82, 84 in the embodiment shown extend in a longitudinal direction, but it should be appreciated that the magazines 82, 84 can be oriented in other manners. For instance, the magazines 82, 84 in other embodiments can be oriented in a V-shaped or L-shaped manner, to name a few examples. As should be recognized, the system 80 addresses the disposal issue by automatically storing used test elements 36 in the waste magazine 84.

In the illustrated embodiment, the transport mechanism 86 includes a transport drum 88. To transport test elements 36, the transport drum 88 rotates in clockwise 90 and counterclockwise 92 directions, as shown in FIG. 5. Between the magazines 82, 84, the drum 88 is able to rotate to a sampling position or orientation 94 where a fluid sample can be collected and analyzed.

As mentioned before, with portable meters, such as portable blood glucose meters, small meter sizes and ease of handling are desirable features. Most users would prefer smaller meters that are able to discretely fit inside a pocket or a purse so that the user is able to perform testing in any situation, such as in a restaurant bathroom or when traveling. One factor affecting size of meters that handle multiple test strips is storage compartment sizes. In previous designs, the storage compartments tended to be rather large and bulky because test elements were stored in a disorderly fashion. The meter transport system 80 in FIG. 5 stores test elements in both the supply 82 and waste 84 magazines in a compact, stacked fashion. This allows the entire system package to have a compact design. In addition, the drum 88 provides a compact as well as effective mechanism to transport test elements 36.

Figure 6:
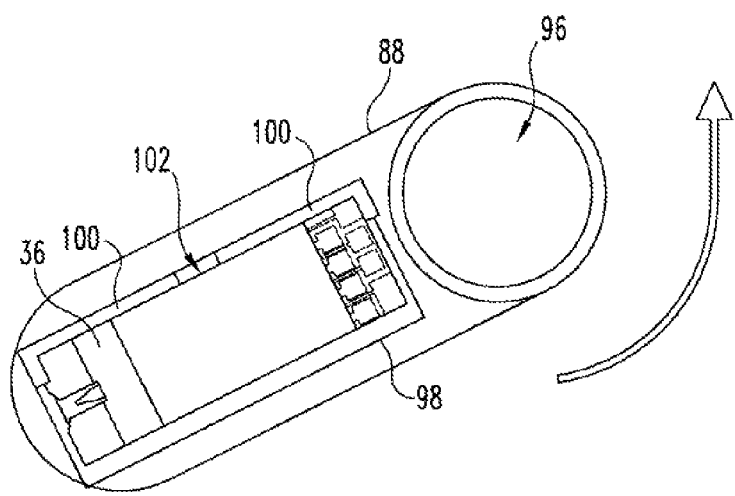
FIG. 6 is a perspective view of a transport drum of the FIG. 5 system.
Figure 7:
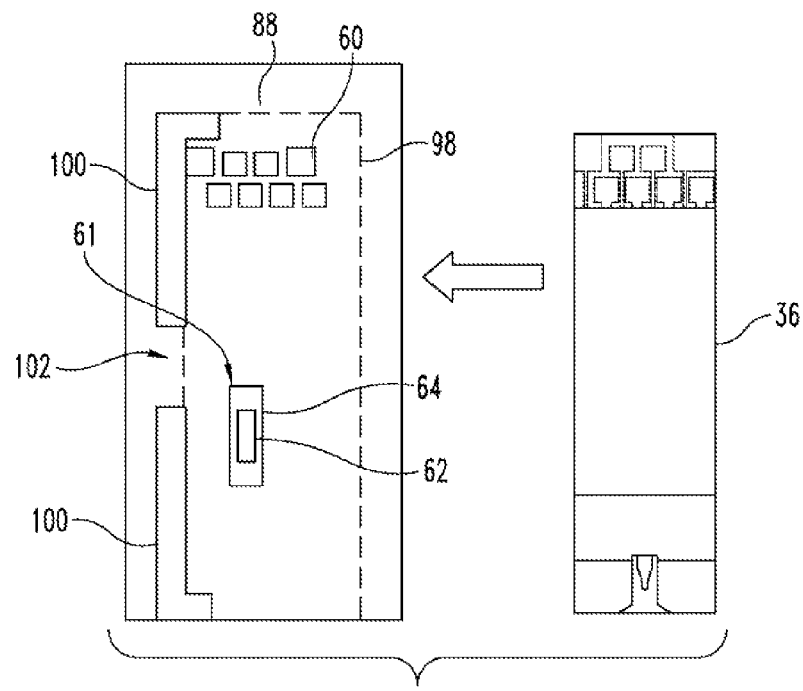
FIG. 7 is a diagrammatic view of a test element being loaded on the FIG. 6 drum.

Turning to FIG. 6, the drum 88 has a cylindrical shape with a hollow interior 96 that is configured to receive the lancet actuation mechanism 61. It is envisioned that the drum 88 can have a different overall shape in other embodiments. For instance, the drum 88 in other forms can have a hexagonal cross-sectional shape or other shapes. The drum 88 has a test element relief notch 98 in which the test element 36 is received when loaded. In the embodiment shown, the notch 98 is in the form of a flat section or indentation on the drum 88, but the notch 98 can be shaped differently in other embodiments. As can be seen in FIG. 7, the notch 98 has contacts 60 for electrically coupling the test element 36 to the meter. At the notch 98, the drum 88 further incorporates the lancet actuation mechanism 61 with the engagement arm 62 that engages the lancet in the test element 36 and guide slot 64 where the engagement arm 62 travels. As mentioned before, the lancet in the test element 36 can be actuated in other manners, and the test element 36 in other forms may not incorporate a lancet.

Along one side of the notch 98, the drum 88 has one or more catch rails 100 that hold the test element 36 in place during transport, as is depicted in FIGS. 6, 7, 8, and 9. Looking at FIG. 9, the rails 100 have retention channels 101 that are configured to retain the test elements 36, and the rails 100 have an overall shape that is L-shaped so as to engage the edges of the test element 36, which tends to minimize damage. In the depicted embodiment, the rails 100 engage generally at the corners of the test elements 36. As should be recognized, the rails 100 in other embodiments can be shaped differently and engage the test elements 36 in other manners. For example, in one form, the rails 100 are integral with the drum 88 so that the rails 100 are generally flush with respect to the outer surface of the drum 88. It is envisioned that other types of holding devices such as clips can be used in other embodiments. In the illustrated embodiment, the rails 100 only partially cover the ends of the test elements 36 so as to not interfere with lancing and fluid collection. As will be explained in greater detail below with reference to FIGS. 10 and 11, the rails 100 in the illustrated embodiment are spaced apart along one side of the test element 36 to form a relief gap 102 that receives a catch 104 on the waste magazine 84.

Figure 10:
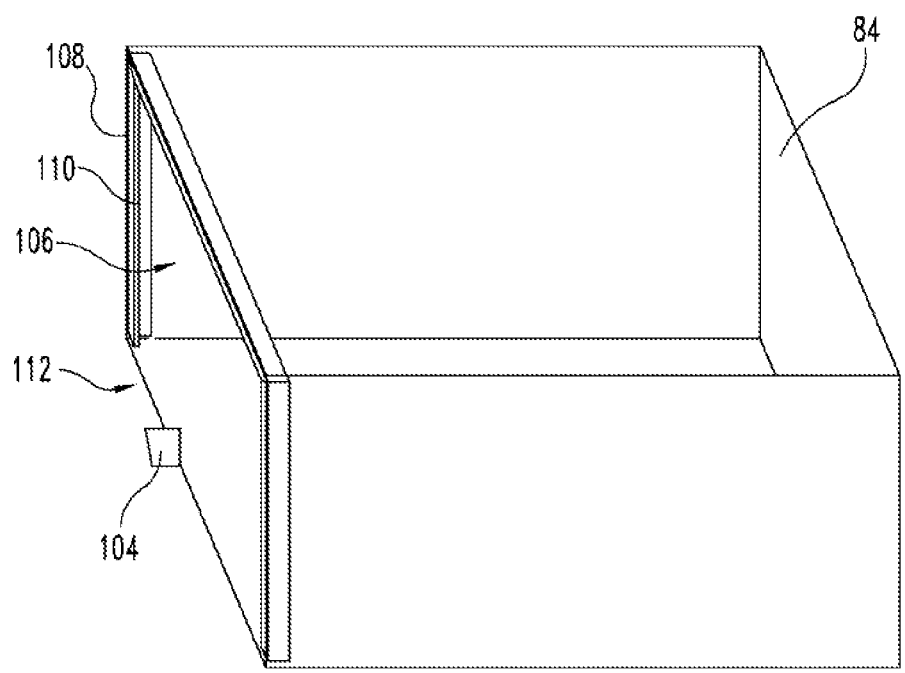
FIG. 10 is a perspective view of a waste magazine for the FIG. 5 system.

Turning to FIG. 10, the waste magazine 84 has a waste receptacle opening 106 that faces the drum 88 and is configured to receive used test elements 36. Around the opening 106, the waste magazine 84 has the catch 104 and a series of rails 108 with channels 110 configured to catch used test elements 36 from the drum 88. The rails 108 are oriented in a U-shaped configuration with the catch 104 located at an open end 112 of the U-shaped rails 108. The catch 104 is made of a resilient material that deflects to receive the test element 36, and once the trailing side of the test element 36 passes the catch 104, the catch 104 returns to its original undeflected state, thereby retaining the test element 36 in the waste compartment 84. The catch 104 can include a spring and/or can be made from a resilient material, such as plastic, to allow deflection of the catch 104.

Figure 11:
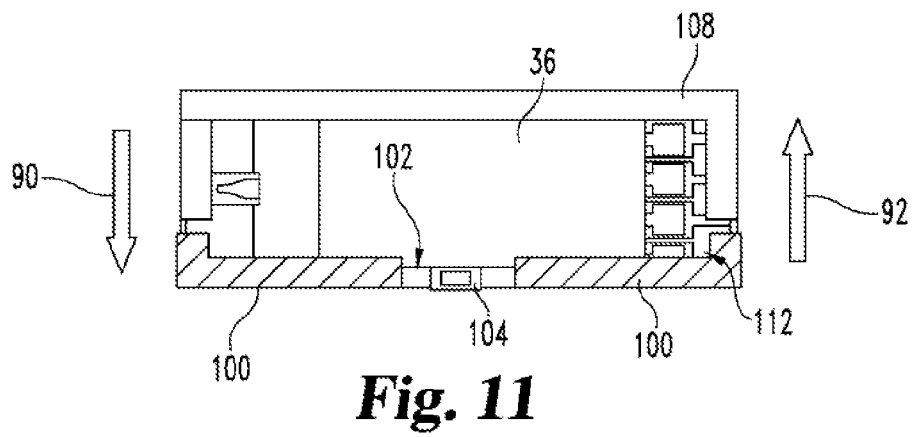
FIG. 11 is a partial cross-sectional view of the FIG. 7 test element being loaded into the FIG. 10 waste magazine.

FIG. 11 illustrates the interface between the rails 100 of the drum 88 and the rails 108 of the waste magazine 84 when a used test element 36 is loaded into the waste magazine 84. Although the drum 88 will be described as being rotated in a specific direction during the various stages, it should be recognized that the drum 88 can be rotated in other combinations of directions at the various stages. As can be seen, when the test element 36 is in the loaded position, the catch 104 is received in the relief gap 102 between the rails 100 on the drum 88. The catch 104 holds the test element 36 within the rails 108 of the waste magazine 84 as the drum 88 rotates back to load another test element 36 from the supply magazine 82.

Figure 8:
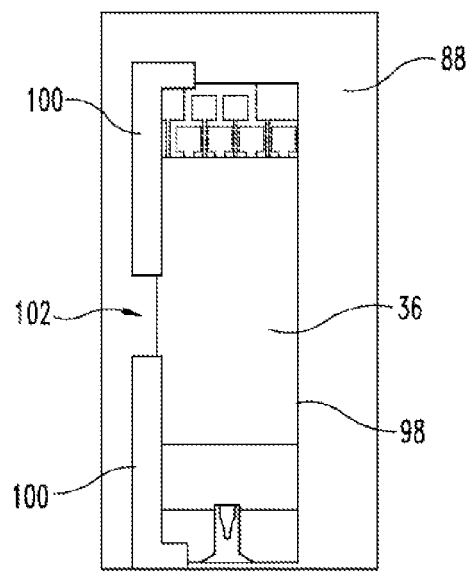
FIG. 8 is a top view of the FIG. 7 test element loaded on the FIG. 6 drum.
Figure 9:
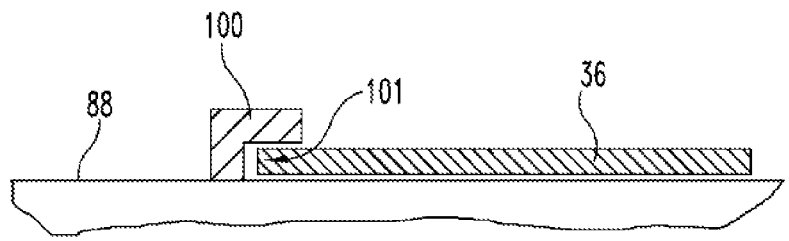
FIG. 9 is a cross-sectional view of the FIG. 7 test element loaded on the FIG. 6 drum.

The operation of the transport system 80 will be initially described with reference to FIGS. 5 and 6. The drum 88 receives a fresh test element 36 from the supply magazine 82 by rotating in a clockwise direction 90 such that the test element relief notch 98 rotates slightly past the opening of the supply magazine 82. As mentioned before, the drum 88 can be manually rotated by the user and/or rotated via a drive mechanism, such as an electric motor. Upon the drum 88 rotating in the counterclockwise direction 92, the rails 100 on the drum 88 catch the top-most test element 36 on the stack of test elements 36 in the supply magazine 82, as is depicted in FIGS. 7, 8, and 9. As the drum 88 continues to rotate, the test element 36 is removed from the supply magazine 82.

The drum 88 then orients the test element 36 at the sampling position 94 (FIG. 5). While at the sampling position 94, the test element 36 collects and analyzes a fluid sample. In one form, the lancet engagement arm 62 (FIG. 7) fires the lancet of the test element 36 so as to form an incision in tissue. Body fluid from the incision is then drawn into the test element 36, and the readings for the analysis are conveyed via the contacts 60 on the drum 88. It is contemplated that in other embodiments, the fluid sample can analyzed with the test element 36 moved to a different position once the fluid sample is collected.

After the fluid sample is analyzed, the now used test element 36 on the drum 88 is transported to the waste magazine 84. In the illustrated embodiment, the drum 88 is rotated in a counterclockwise direction 92 (FIG. 5) in order to load the used test element 36 into the waste magazine 84. The leading side of the test element 36, which is opposite the rails 100 on the drum 88, pushes against the top-most test element 36 in the waste magazine 84 at a slight angle. This results in the test element 36 in the waste magazine being pushed slightly backwards to make room for the test element 36 on the drum 88. In addition, the catch 104 on the waste magazine 84 deflects slightly. When the drum 88 rotates further, the test element 36 on the drum 88 slides into the rails 108 of the waste magazine 84. The test element 36 continues to slide into the rails 108 of the magazine 84 as the drum 88 rotates until the catch 104 of the waste magazine 84 is received into the relief gap 102 between the rails 100 on the drum 88. At that point, the catch 104 returns to its original undeflected state so that the test element 36 is held within the waste magazine 84. Afterwards, the drum 88 is rotated in a clockwise direction 90 (FIG. 5) such that the catch 104 retains the test element 36 in the waste magazine 84. The same stages are repeated for testing additional fluid samples, and once all of the test elements 36 have been used, the user can dispose of the magazine 84 and/or other various components of the system 80 so as to minimize the risk of hazardous waste exposure.

Figure 12:
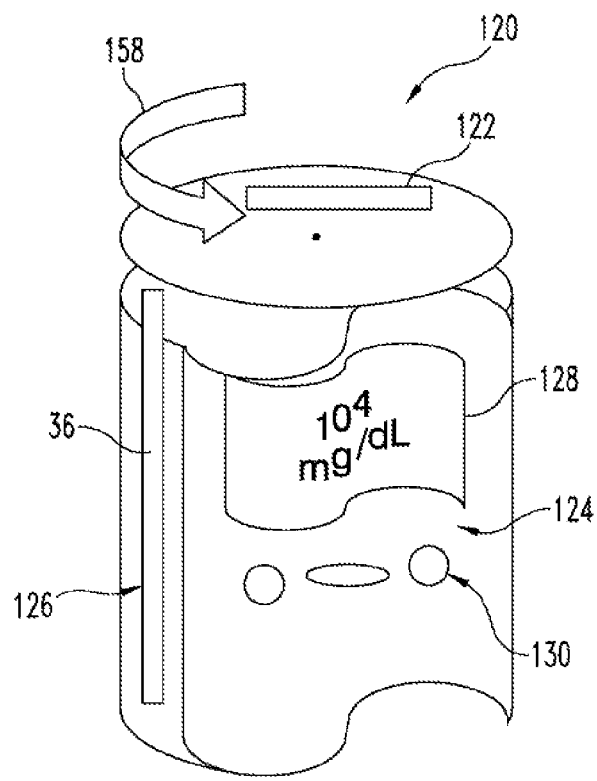
FIG. 12 is a perspective view of a meter system according to a further embodiment.
Figure 13:
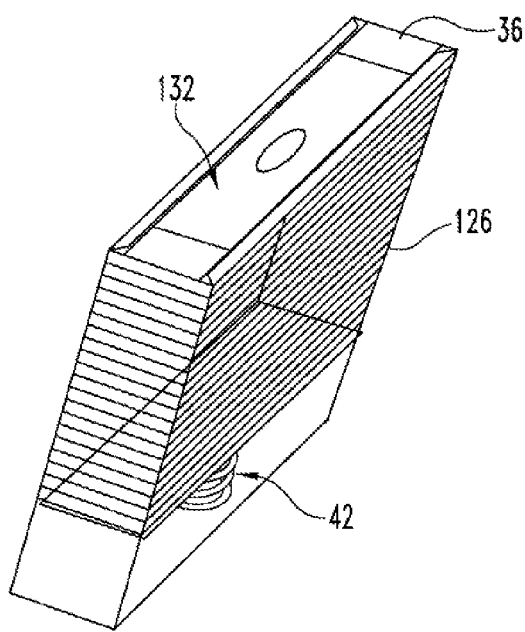
FIG. 13 is a perspective view of a magazine for the FIG. 12 meter system.

A meter system 120 with a transport system 122 for transporting test elements 36 according to another embodiment is illustrated in FIG. 12. As shown, the meter system 120 includes a meter 124, a supply magazine 126 that contains a stack of unused test elements 36, and the transport system 122 that transports test elements 36 from the magazine 126 to the meter 124. As will be described in greater detail below, the transport system 122 in the depicted embodiment is generally disc-shaped and the disc spins to transport the test elements 36. As will be appreciated, the transport system 122 in the illustrated embodiment provides a compact and reliable device for transporting test elements 36.

Figure 14:
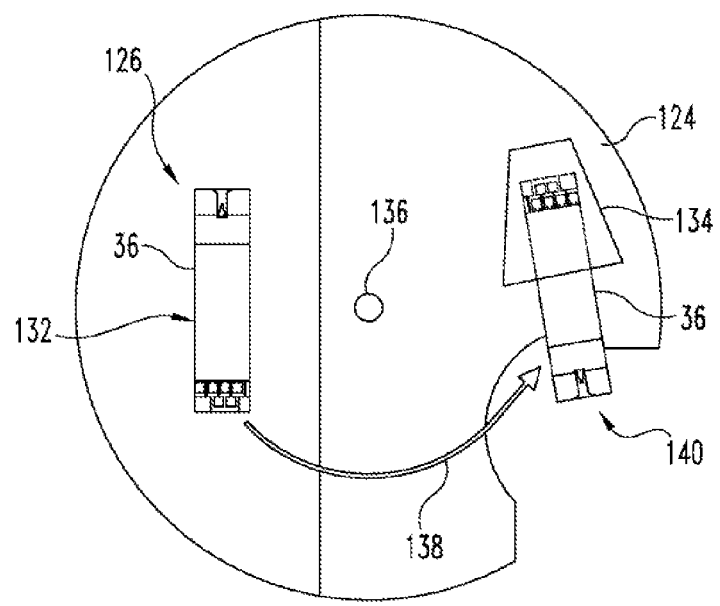
FIG. 14 is a top view of the FIG. 12 meter system with its transport disc removed.

The meter 124 includes an output device 128 in the form of a display for displaying readings and an input device 130 in the form of one or buttons. Like the previous embodiments, the magazine 126 includes a spring 42 that biases the test elements 36 towards a supply opening 132. The magazine 126 can further include a desiccant to maintain low humidity levels in the magazine 126. Looking at FIG. 14, the meter 124 and the magazine 126 are generally oriented in a side-by-side fashion. The meter 124 has a female test element connector 134 in which the end of the test element 36 that contains contacts is received. Inside, the connector 134 in one embodiment can have the lancet engagement arm 62 for actuating the lancet in the test element 36. Further, the meter 124 has a shaft 136 that is used to rotate the transport system 122, as will be explained in greater detail below. In one form, the shaft 136 is coupled to a motor inside the meter 124 so that the meter 124 is able to automatically rotate the transport system 122. In another form, the shaft 136 merely provides a pivot point when the user manually rotates the transport system 122. As depicted by arrow 138 in FIG. 14, the transport system 122 rotates in a manner such that one of the test elements 36 from the magazine 126 is inserted into the female connector 134. Near the female connector 134, the meter 124 has a relief notch 140 in which the collection end of the test element 36 extends to collect fluid from an incised body part, such as a finger.

Figure 15:
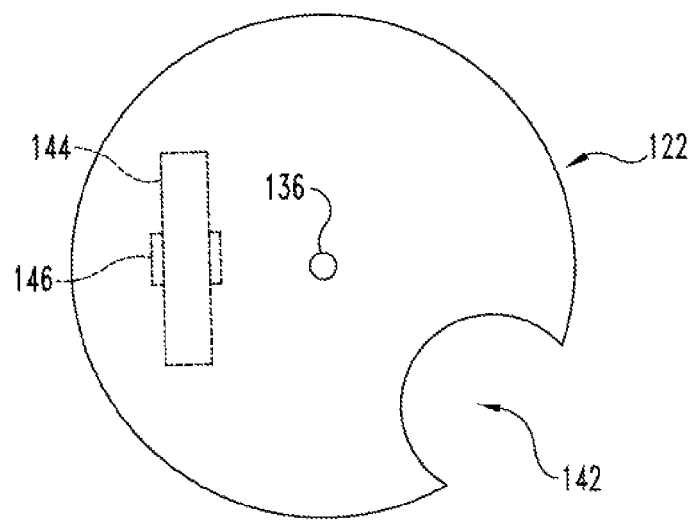
FIG. 15 is a top view of the transport disc for the FIG. 12 meter system.
Figure 16:
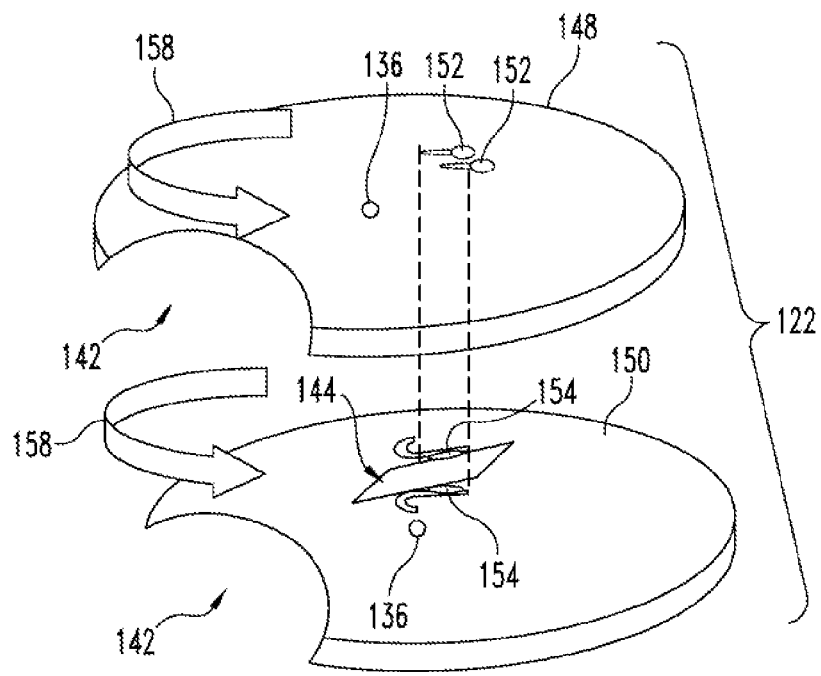
FIG. 16 is an exploded view of the FIG. 15 transport disc.

Turning to FIGS. 15 and 16, the transport system 122 likewise has a relief notch 142 that is configured to prevent interference with the test element 36 when collecting a fluid sample. Again, the shaft 136 from the meter 124 is coupled to the transport system 122 for rotating of the transport system 122. The transport system 122 includes a test element cavity or recess 144 in which the test element 36 is received and a gripping mechanism 146 for gripping the test element 36 when in the test element cavity 144. In the embodiment illustrated in FIG. 16, the transport system 122 is in the form of a composite disc with a first (or top) layer or disc 148 and a second (or bottom) layer or disc 150 that is sandwiched between the first disc 148 and the meter 124. The discs 148, 150 are able to both move independently with respect to one another and in unison together. It is contemplated that the transport system 122 can be configured differently in other embodiments and can engage the test element 36 in other manners. For instance, instead of two discs, the transport system 122 in other embodiments can include one or mores discs that have test element engagement rails similar to the above-discussed embodiments that hold the test element 36 during transport.

Figure 17:
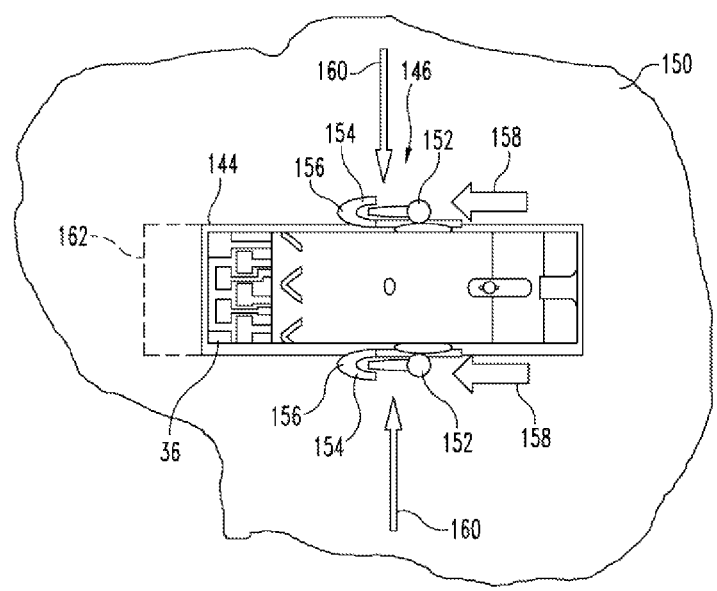
FIG. 17 is an enlarged view of a test element being loaded onto the FIG. 15 transport disc.

Looking at FIG. 16, the underside of the top disc 148, which faces the bottom disc 150, has one or more lock pins 152 that are configured to engage on or more corresponding grip members 154 on the bottom disc 150. In the illustrated embodiment, the top disc 148 includes a pair of lock pins 152 that are configured to engage a pair of grip members 154 that are located on opposite sides of the test element cavity 144. However, in other embodiments, the transport system 122 can include more or less lock pins 152 and grip members 154 than are shown. The lock pins 152 are generally rigid, while the grip members 154 are flexible. With reference to FIG. 17, the grip members 154 each have hooked shaped ends that form catches 156 that are configured to engage the lock pins 152.

As noted above, a motor in the meter 124 can automatically rotate the top disc 148 and/or the user can manually rotate the top disc 148. When the top disc 148 is rotated in a counterclockwise direction 158, the lock pins 152 engage the catches 156 on the grip members 154, which in turn compresses the grip members 154 in an inward direction 160. Consequently, the grip members 154 grip the sides of the test element 36, thereby holding the test element in the transport system 122. Holding the sides of the test elements in such a manner helps to reduce damage of the test element 36 during transport. Once the lock pins 152 on the top disc 148 engage the catches 156, the bottom disc 150 starts moving in the counterclockwise direction 158 so as to transport the test element 36 to the test element connector 134. When in the test element cavity 144, the test element 36 can be angled slightly so that the end of the test element 36 extends from the underside of the bottom disc 150 so that the test element 36 is able to engage the connector 134. Alternatively or additionally, the bottom disc 150 can incorporate a beveled cavity 162 at one end of the test element cavity 144 that exposes the connection end of the test element 36 to the connector 134 so as to facilitate the connection between the test element 36 and the connector 134. Once the test element 36 reaches the connector 134, the end of the test element 36 containing the contacts is inserted into the connector 134 to engage the spring-biased contacts in the connector 134, thereby forming an electrical connection between the test element 36 and the meter 124. Afterwards, the top disc 148 is rotated in a clockwise direction (either manually or automatically), which disengages the lock pins 152 from the grip members 154. With the lock pins 152 removed, the grip members 154 release the test element 36 such that the test element 36 remains in the connector 134.

A technique for loading test elements 36 onto the meter 124 in the meter system 120 will be initially described with reference to FIGS. 12, 14, 15, and 16. During loading, the bottom disc 150 is rotated so that the test element cavity 144 is positioned over the supply opening 132 of the magazine 126. In one form, the bottom disc 150 has a spring that biases the bottom disc 150 to a position where the test element cavity 144 is positioned over the magazine. In other forms, the bottom disc 150 can be manually positioned by the user and/or automatically positioned via a motor. The spring 42 in the magazine 126 pushes the top-most test element 36 into the test element cavity 144. Looking at FIGS. 16 and 17, the top disc 148 is rotated in the counterclockwise direction 158 such the lock pins 152 engage the grip members 154. Once the lock pins 152 engage the grip members 154, the grip members 154 squeeze against the side edges of the test elements 36 to hold the test element 36 in the test element cavity 144. As the top disc 148 continues to rotate, the engagement of the lock pins 152 with the grip members 154 causes the bottom disc 150 to rotate in unison with the top disc 148. The bottom surface of the bottom disc 150 holds the remaining test elements 36 in the magazine 126 as the transport system 122 rotates. The transport system 122 continues to rotate in the counterclockwise direction until the connection end of the test element 36 is inserted into the connector 134 of the meter 124. At that point, the contacts in the connector 134 engage the contacts on the test element 36.

Once the test element 36 is connected to the connector 134, the top disc 148 rotates in a clockwise direction, thereby disengaging the lock pins 152 from the grip members 154. The now disengaged lock pins 152 release the test element 36 in the connector 134. The bottom disc 150 is then rotated in a clockwise direction so that the test element cavity 144 is positioned over the magazine 126. The bottom disc 150 can be rotated in the clockwise direction manually by the user and/or automatically, such as via a return spring or a motor. Both discs 148, 150 are oriented in a manner such that their relief notches 142 align with the relief notch 140 in the meter 124 so as to permit sampling by the test element 36. Afterwards, the lancet in the test element 36 can be fired to form an incision, and the fluid from the incision can be analyzed with the test element 36. The results from the analysis can be outputted via the output device 128 on the meter 124. Once the test element 36 is used, the test element can be manually discarded by the user. It is contemplated that the test element 36 can be automatically discarded in other embodiments. After the used test element 36 is discarded, an unused test element 36 from the magazine 126 can be loaded in the same fashion as described above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents, and patent applications cited in this specification are herein incorporated by reference as if each individual publication, patent, or patent application was specifically and individually indicated to be incorporated by reference as set forth in its entirety herein.

What is claimed is:

1. A meter system, comprising:
   a supply magazine storing one or more test elements in a stacked manner;
   a meter having a load cavity;
   a transport mechanism to transfer the test elements from the supply magazine to the load cavity of the meter, the transport mechanism including a shuttle defining a test element opening in which the test elements are received, the shuttle being configured slide from a first position where the element opening is disposed over the magazine to a second position where the test element opening is disposed over the load cavity, and a stabilizer arm configured to hold the test elements in the test element opening during sliding of the shuttle, the stabilizer arm being configured to push the test elements into the load cavity of the meter when the shuttle is at the second position;
   the magazine having an outlet opening, and a spring biasing the test elements towards the outlet opening of the magazine; and
   the stabilizer arm being configured to apply a force against the test elements in the magazine that is less than a force applied against the test elements by the spring of the magazine to facilitate loading of the test elements into the test element opening of the shuttle.

2. The system of claim 1, wherein the stabilizer arm is configured to deflect to an extent that allows one of the test elements to be received in the test element opening of the shuttle.

3. The system of claim 1, wherein the meter includes an ejection mechanism to eject the test elements from the load cavity.

4. The system of claim 3, wherein the ejection mechanism includes:
   a series of rails defining the load cavity of the meter;
   an ejection button coupled to the rails; and
   the rails being slidably mounted to the meter such that when the ejection button is pressed one of the test elements located in the load cavity moves in an ejection direction.

5. The system of claim 4, wherein the ejection button is spring biased so that the ejection button returns to an initial position once the ejection button is released.

6. The system of claim 1, further comprising:
   the load cavity having one or more contacts that electrically couple the test elements to the meter; and
   the stabilizer arm is configured to stably position the test elements against the contacts in the load cavity.

7. The system of claim 1, further comprising:
   the test elements being each a lancet integrated test element that includes
   a test strip configured to analyze body fluid, and
   a lancet coupled to the test strip for forming an incision;
   the load cavity including a lancet actuation mechanism configured to fire the lancet; and
   the stabilizer arm being configured to stably position the lancet integrated test element when the lancet actuation mechanism fires the lancet.

8. The system of claim 1, wherein the stabilizer arm includes a leaf spring.

* * * * *